United States Patent [19]

Sarngadharan et al.

[11] Patent Number: 4,843,011
[45] Date of Patent: Jun. 27, 1989

[54] MONOCLONAL ANTIBODIES FOR BINDING HTLV-III PROTEINS, AND CELL LINES FOR THEIR PRODUCTION

[75] Inventors: Mangalasseril G. Sarngadharan, Vienna, Va.; Fulvia di Marzo Veronesé, Washington, D.C.; Robert C. Gallo, Bethesda, Md.

[73] Assignee: Akzo N.V., Arnhem, Netherlands

[21] Appl. No.: 816,573

[22] Filed: Jan. 3, 1986

Related U.S. Application Data

[63] Continuation-in-part of Ser. No. 761,489, Aug. 1, 1985, abandoned, which is a continuation-in-part of Ser. No. 756,237, Jul. 18, 1985, abandoned.

[51] Int. Cl.$^4$ .................... G01N 33/577; C12N 15/00
[52] U.S. Cl. .................... 435/240.27; 435/5; 435/7; 435/68; 435/810; 435/172.2; 436/548; 436/808; 436/809; 436/811; 530/387; 530/808; 530/809; 935/95; 935/100; 935/104; 935/106; 935/107; 935/108; 935/110
[58] Field of Search .................... 435/5, 7, 68, 240.27, 435/810, 172.2; 530/387, 808, 809; 436/548, 811, 808, 809; 935/95, 100, 104, 106–108, 110

[56] References Cited

U.S. PATENT DOCUMENTS

| | | | |
|---|---|---|---|
| 4,520,113 | 5/1985 | Gallo et al. | |
| 4,629,783 | 12/1986 | Cosand | 530/324 |
| 4,704,357 | 11/1987 | Mitsuya et al. | 435/32 |
| 4,708,818 | 11/1987 | Montagnier et al. | 435/5 |
| 4,725,669 | 2/1988 | Essex et al. | 530/322 |
| 4,735,896 | 4/1988 | Wang et al. | 435/5 |
| 4,752,565 | 6/1988 | Folks et al. | 435/5 |
| 4,755,457 | 7/1988 | Robert-Guroff et al. | 435/5 |

OTHER PUBLICATIONS

Kanki et al., "Serologic Identification and Characterization of a Macaque T-Lymphotropic Retrovirus Closely Relates to HTLV-III", Science, 228(06/07/85) 1199–1201.
Barin et al., "Virus Envelope Protein of HTLV-III Represents Major Target Antigen for Antibodies in AIDS Patients", Science, 228(05/31/85) 1094–1096.
Sarngadharan et al., "Antibodies Reactive with Human T-Lymphotropic Retroviruses (HTLV-III) in the Serum of Patients with AIDS", Science, 224(05/04/84) 506–508.
Robey et al., "Characterization of Envelope and Core Structural Gene Products of HTLV-III with Sera from AIDS Patientsd", Science, 228 (05/03/85) 593–595.
F. Veronese et al., "Monoclonal Antibodies Specific for P24, the Major Core Protein of Human T-Cell Leukemia Virus Type III", Proc. Natl. Acad. Sci., USA, vol. 82, Aug. 1985.
Popovic et al., "Detection, Isolation, and Continuous Production of Cytopathic Retroviruses (HTLV-III) from Patients with AIDS and Pre-AIDS", Science, May 4, 1984, 224:497–500.
Gallo et al., "Frequent Detection and Isolation of Cytopathic Retroviruses (HTLV-III) from Patients with (List continued on next page.)

Primary Examiner—Christine M. Nucker
Attorney, Agent, or Firm—William M. Blackstone

[57] ABSTRACT

Monoclonal antibodies, and hybridoma cell lines for their production, that bind with a high degree of specificity proteins associated with HTLV-III virus are presently disclosed. In particular, transmembrane envelope glycoprotein gp41 (41,000 dalton molecular size), major core antigen p24 (24,000 dalton molecular size), and p17 protein (17,000 dalton molecular size) are disclosed. The proteins to which the present monoclonal antibodies respond are essentially antigenically distinct from HTLV-I and HTLV-II. SVM-16 is an IgM monoclonal antibody, SVM-23 is an IgG$_2$ monoclonal antibody, and SVM-26 is an IgG$_1$ monoclonal antibody, all of which bind to p24. SVM-25 is an IgG$_1$ monoclonal antibody binding gp41, and SVM-33 is an IgG$_1$ monoclonal antibody binding p17. All the monoclonal antibodies of the present invention are produced in hybridoma cells prepared by fusing myeloma cells with spleen cells from mammals, such as mice, immunized with lysates of purified virus.

13 Claims, 7 Drawing Sheets

OTHER PUBLICATIONS

AIDS and at Risk for AIDS", *Science,* May 4, 1984, 224:500-503.

Schupbach et al., "Serological Analysis of a Subgroup of Human T-Lymphotropic Retroviruses (HTLV-III) Associated with AIDS", Science, May 4, 1984, 224:503-505.

Sarngadharan et al., "Antibodies Reactive with Human T-Lymphotropic Retroviruses (HTLV-III) in the Serum of Patients with AIDS", Science, May 4, 1984, 224:506-508.

Schupbach et al., "Antigens on HTLV-Infected Cells Recognized by Leukemia and AIDS Sera are Related to HTLV Viral Glycoprotein", Science, May 11, 1984, 224:607-609.

Ratner et al., "Complete Nucleotide Sequence of the AIDS Virus, HTLV-III", *Nature,* Jan. 24, 1985, 313:277-284.

Safai et al., "Seroepidemiological Studies of Human T-Lymphotropic Retrovirus Type III in Acquired Immunodeficiency Syndrome", *The Lancet,* Jun. 30, 1984, pp. 1438-1440.

Kitchen et al., "Aetiology of AIDS-Antibodies to Human T-Cell Leukaemia Virus (Type III) in Haemophiliacs", *Nature,* vol. 312, Nov. 22, 1984, pp. 367-369.

Extracts tested include;
A) H9-HTLV-III
B) H9 not infected
C) HTLV-III

Sera tested include:
A) Mouse antiserum to HTLV-III p24
B) Prebleed
C-D-E-F) Supernatant from A173, B69 M16 and M23

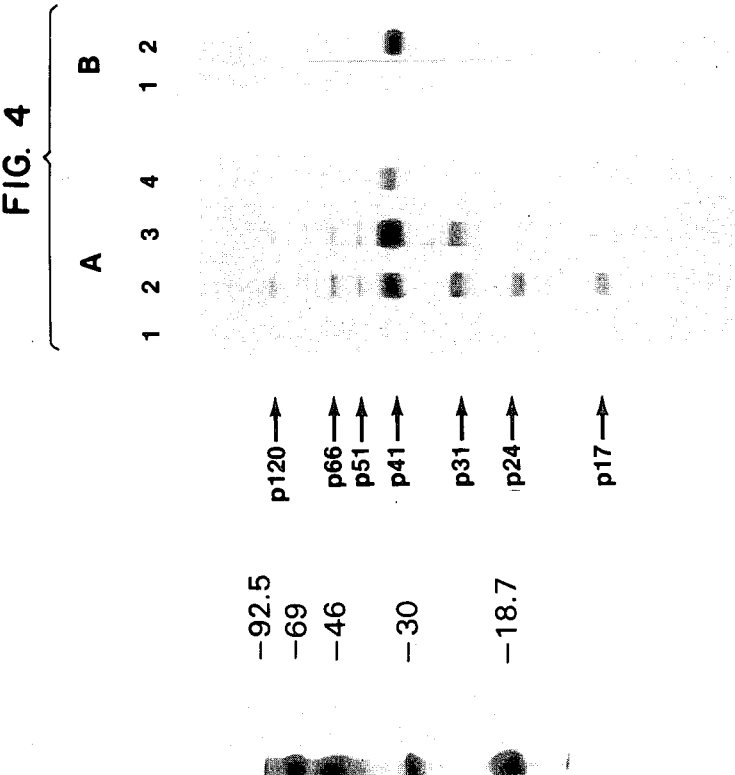
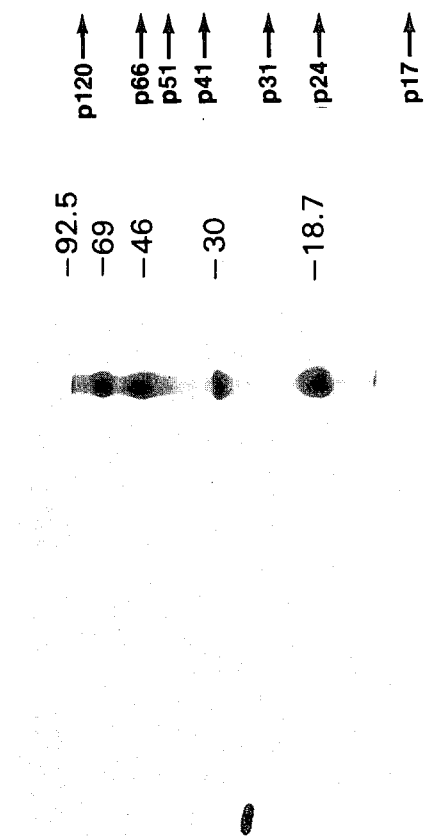
FIG. 3
FIG. 4
Extracts tested included:
A) HTLV-III
B) HTLV-I
C) HTLV-II
D-E) HTLV-I and II producing cells
F) B lymphoblastoid line
G) Mitogen stimulated human T cells

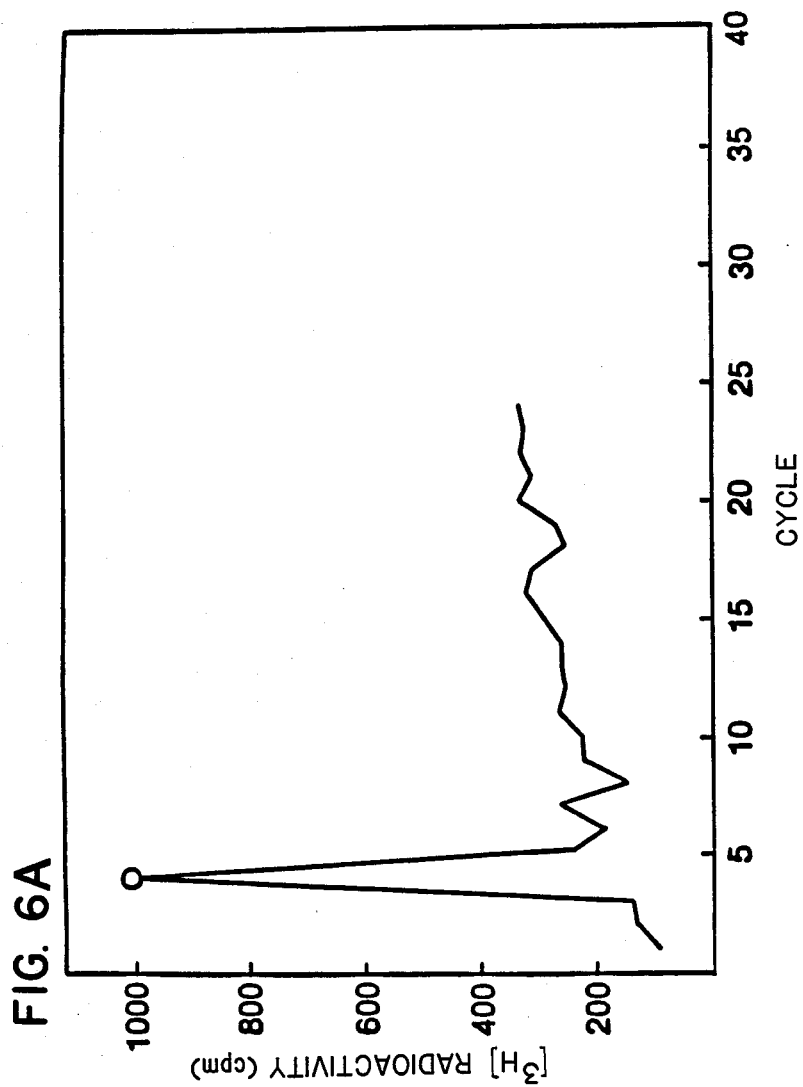

MONOCLONAL ANTIBODIES FOR BINDING HTLV-III PROTEINS, AND CELL LINES FOR THEIR PRODUCTION

This application is a continuation-in-part application of presently pending U.S. Ser. No. 06/761,489, filed Aug. 1, 1985, which is a continuation-in-part application of U.S. Ser. No. 06/756,237, filed July 18, 1985.

This invention relates to monoclonal antibodies specific for proteins that characterize HTLV-III, the virus that has been identified with acquired immuno deficiency syndrome (AIDS). In particular, the invention relates to monoclonal antibodies that demonstrate immune reactivity with a 41,000 dalton protein (p41), which we have identified as a transmembrane envelope glycoprotein of the HTLV-III virus, a 24,000 dalton (p24) protein, which is a major core protein of the virus, and a 17,000 dalton (p17) protein, all of which are specific antigens that identify HTLV-III virus and demonstrate little or no cross-reactivity with HTLV-I and HTLV-II viruses or their lysates. These antibodies provide a means for directly detecting the virus in the sera, blood or blood products of AIDS patients or HTLV-III carriers. Such methods are an important advance over the indirect antibody detection methods presently used. Methods based on antibody detection give false negatives if there is a complete failure of the patient's immune system, as no antibodies are produced. The present antibodies provide a positive indication of the presence of the virus at any stage of the disease in a patient or in a healthy carrier of virus.

STATEMENT OF DEPOSIT

Cell lines corresponding to the present invention have been deposited in the American Type Culture Collection, 12301 Parklawn Drive, Rockville, Md. 20852 prior to filing this patent application. Cell lines MH-SVM-23, MH-SVM-25, and MH-SVM-26 were deposited on July 15, 1985 and assigned ATCC Deposit Nos. HB8870, HB8871, and HB8872, respectively. Cell line MH-SVM-16 was deposited on August 1, 1985 and assigned ATCC Deposit No. HB8880. Cell line MH-SVM-33 was deposited on December 16th, 1985 and assigned ATCC Deposit No. HB8975.

BACKGROUND OF THE INVENTION

Incorporated herein, by reference, in their entirety are U.S. Pat. No. 4,520,113, issued May 28, 1985 to Gallo et al and the article Di Marzo Veronese et al, "Monoclonal Antibodies Specific for P24, the Major Core Protein of Human T-Cell Leukemia Virus Type III," *Proc. Natl. Acad. Sci. USA*, Volume 82, to be published August 1, 1985; Popovic et al, "Detection, Isolation, and Continuous Production of Cytopathic Retroviruses (HTLV-III) from Patients with AIDS and Pre-AIDS," *Science*, May 4, 1984, 224:497–500; Gallo et al, "Frequent Detection and Isolation of Cytopathic Retroviruses (HTLV-III) from Patients with AIDS and at Risk for AIDS," *Science*, May 4, 1984, 224:500–503; Schüpbach et al, "Serological Analysis of a Subgroup of Human T-Lymphotropic Retroviruses (HTLV-III) Associated with AIDS," *Science*, May 4, 1984, 224:503–505; Sarngadharan et al, "Antibodies Reactive with Human T-Lymphotropic Retroviruses (HTLV-III) in the Serum of Patients with AIDS," *Science*, May 4, 1984, 224:506–508; Schüpbach et al, "Antigens on HTLV-Infected Cells Recognized by Leukemia and AIDS Sera are Related to HTLV Viral Glycoprotein," *Science*, May 11, 1984, 224:607–609; Ratner et al, "Complete Nucleotide Sequence of the AIDS Virus, HTLV-III," *Nature*, Jan. 24, 1985, 313:227–284; and Safai et al, "Sero Epidemiological Studies of Human T-Lymphotropic Retrovirus Type III, in Acquired Immuno Deficiency Syndrome," *The Lancet*, June 30, 1984 pp. 1438–1440. These incorporated references, and the references in the copending application cited herein, provide a full description of the background of this invention, the problems that are presently solved, and the uses for the presently claimed cell lines and monoclonal antibodies. They are also incorporated to define the terms and describe the methods and procedures used in the present invention.

The human T-cell leukemia viruses are a family of T lymphotropic retroviruses etiologically associated with the alteration of T cell functions, leading to abnormal proliferation (leukemia) or depletion (immunosuppression) of T lymphocytes. The previous most common isolate, which was also the first isolate, HTLV-I, was obtained from an American patient with an aggressive form of mature T-cell lymphoma (23' and reviewed in 24'). The second isolate, HTLV-II, was first isolated from a patient with a T-cell variant of hairy cell leukemia (25' and reviewed in 24'). HTLV-III has been frequently detected and isolated from patients with acquired immunodeficiency syndrome (AIDS) or with signs and symptoms that frequently precede AIDS (AIDS-related conditions [ARC]) (1'). Isolates closely related or identical to HTLV-III have been obtained by investigators in other laboratories (2',3',26'). AIDS is a newly described disease characterized by severe immune depression with depletion of the OKT4+ subset of T lymphocytes (27',28') and is accompanied by multiple opportunistic infections or neoplasias (26'). Common biological features of all members of the HTLV family include their preferred tropism for T cells (1',30',31'), and morphologic appearance of budding and early forms of the virus under electron microscopy.

Even though HTLV-III is antigenically distinct from HTLV-I and -II, it shares a number of determinants (32',33') and some nucleotide sequence homology (34',35'). Like the other two isolates, HTLV-III has a major structural protein with a molecular weight of about 24,000 (p24) (33'), and a reverse transcriptase with a molecular weight of 100,000, but the protein homologous to p19 is somewhat smaller, having a molecular weight of about 17,000 (p17) (7', and our unpublished data). Another difference involves the in vitro transmission of the virus to primary human T-cells. Whereas HTLV-I and -II can transform some of these cells and be propagated indefinitely in them (30',31'), HTLV-III is only transiently produced in these cells (1'). The problem has been overcome by propagating the virus in a human neoplastic cell line (HT) (1').

Isolation of the AIDS agent has enormous clinical implications because it allows the possibility of developing specific assays to identify HTLV-III infection, the first step in interrupting its spread. The correlation between the presence of antibodies to HTLV-III proteins and AIDS has identified this virus as the causative agent for AIDS (7',8',16'). However, the only reported antibody reagent for subtyping HTLV-III before the present invention is a polyclonal antibody to p24 (33'), which reacts with several different lysate fragments and also exhibits low level cross-reactivity to HTLV-I and -II.

Human T-cell leukemia virus type-III (HTLV-III) has been isolated from several patients with acquired immune deficiency syndrome (AIDS), AIDS-related complex (ARC) and from asymptomatic carriers of infection (1'). Other retroviral isolates from similar sources known as lymphadenopathy associated virus (LAV) (2') and by other names (3') appear to be closely similar to various isolates of HTLV-III, as evidenced by the nucleotide sequences of the respective proviral DNAs (4',5') and endonuclease restriction maps (6'). Epidemiological data on prevalence of antibodies to HTLV-III among various AIDS-risk groups (7',8') and recovery of HTLV-III at high frequency from the same risk groups (1') indicate that HTLV-III is the etiological agent of AIDS. This is further strengthened by the development of AIDS in individuals not belonging to any known risk groups solely as a consequence of blood transfusion (9'); by the observed tropism of the virus for OKT4+ lymphocytes in vitro, and by the profound cytopathic effect of the virus on the OKT4+ lymphocytes both in vitro and in vivo (10'); and by the frequent and reproducible isolation of the virus from semen, saliva and blood of patients with AIDS, ARC and those at risk for these conditions (1',11').

SUMMARY OF THE INVENTION

Monoclonal antibodies, and hybridoma cell lines for their production, that bind with a high degree of specificity proteins associated with HTLV-III virus are presently disclosed. In particular, transmembrane envelope glycoprotein gp41 (41,000 dalton molecular size), major core antigen p24 (24,000 dalton molecular size), and p17 protein (17,000 dalton molecular size) are disclosed. The proteins to which the present monoclonal antibodies respond are essentially antigenically distinct from HTLV-I and HTLV-II. SVM-16 is an IgM monoclonal antibody, SVM-23 is an $IgG_2$ monoclonal antibody, and SVM-26 is an $IgG_1$ monoclonal antibody, all of which bind to p24. SVM-25 is an $IgG_1$ monoclonal antibody binding gp41, and SVM-33 is an $IgG_1$ monoclonal antibody binding p17. All the monoclonal antibodies of the present invention are produced in hybridoma cells prepared by fusing myeloma cells with spleen cells from mammals, such as mice, immunized with lysates of purified virus.

DETAILED DESCRIPTION OF THE INVENTION

Figure 2:
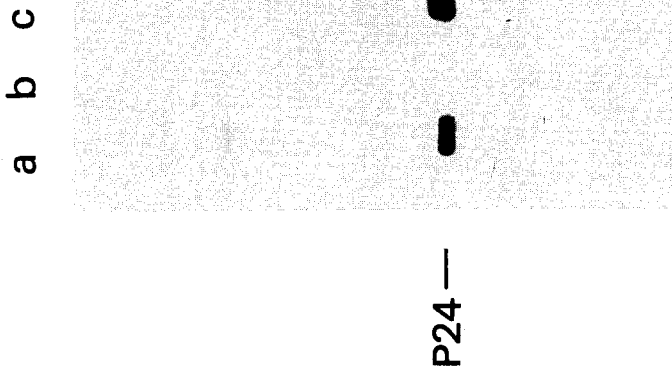

Immunological assays using the Western blot technique (12') have identified several proteins in HTLV-III preparations as major targets of antibody reaction with sera of patients with AIDS and those carrying HTLV-III infection (7',13'). Most high titer sera from AIDS and ARC patients and healthy homosexuals at risk react against HTLV-III proteins of molecular weights 120, 66, 51, 41, 31, 24, and 17K (7',13'). However, the antigen most consistently correlated with sero-positivity to HTLV-III is gp41 (7'). Representative results are given in FIG. 5A. Less frequently, p24, the major HTLV-III core protein, was the only antigen recognized. This difference may have a bearing on the level of intracellular viral replication and/or exposure of viral antigens as a result of the lytic activity on the target cell. Gp41 is both the most consistently detected antigen and the most persistent, being present even at late stages of the disease.

We presently disclose the production and characterization of the first series of hybridomas secreting monoclonal antibodies to HTLV-III gp41, a transmembrane envelope glycoprotein; p24, the major core protein; and p17.

The following examples and procedures are provided to illustrate the methods for obtaining antibodies, the antibodies and their use. They are not, however, intended to limit the invention, which extends to the full scope of the appended claims. The various alternative methods for each step in the disclosed examples are intended to be included as part of the invention. For example, the various known procedures for making hybridomas and the antibody producing cells and myeloma cells from a variety of sources may be used, as long as HTLV-III determinants comprise the antigen for inducing an immune response.

PREPARATION OF MONOCLONAL ANTIBODY

BALB/c mice (Charles River Breeding Lab., Inc., Kingston, N.Y., USA) were immunized with successive intraperitoneal inoculations of detergent lysates prepared from sucrose density gradient purified HTLV-III (100 μg) emulsified in complete Freund's adjuvant for the first inoculation and, beginning one week later, incomplete adjuvant for the following four boosters given one week apart. Three days following a final intraperitoneal booster with disrupted virus in phosphate buffer saline (PBS), splenic lymphocytes were fused with the NS-1 mouse myeloma line (ATCC). The fusion procedure, cell culturing, determination of immunoglobulin subclass secretion and cloning of hybridoma lines were essentially the same procedures as already described in the literature (Kohler and Milstein, *Nature*, 1975, 256:495), (14',36'). Mouse ascitic fluid containing monoclonal antibodies was prepared as described (14').

ELISA

Supernatant fluids of hybrids obtained were screened by enzyme-linked immunoassay (ELISA) (7') using disrupted HTLV-III as antigen. Wells of 96-well plastic trays were coated overnight with a lysate of density-banded HTLV-III at 0.5 μg protein per well in 100 μl of 50 mM sodium bicarbonate buffer, pH 9.6. The wells were then washed once with distilled water and incubated overnight at 4° C. with 100 μl of each individual hybrid cell supernatant fluid to be tested. The wells were then washed three times with 0.05% Tween 20 (polyoxyethylene sorbitan monolaurate, Sigma Chem, St. Louis, Mo., USA) in PBS and incubated for 1 hour at room temperature with affinity-purified, peroxidase-labeled goat antibody to mouse immunoglobulin G (Kirkegaard and Perry Labs., Inc., Gaithersburg, Md., USA) at a dilution of 1:1000 in PBS with 1% normal goat serum. The wells were washed four times with 0.05% Tween 20 in PBS and four times with PBS and reacted with 100 μl of the substrate mixture containing 0.05% orthophenylenediamine and 0.005% hydrogen peroxide in phosphate-citrate buffer, pH 5.0. The reaction was stopped by the addition of 50 μl of 4N $H_2SO_4$ and the color yield was measured with a Litton Bionetics, Inc., ELISA Spectrophotometer at 492 nm. Absorbance readings greater than 10 times the negative control readings were taken as positive.

WESTERN BLOTS AND SOLID PHASE RADIOIMMUNOASSAY

Lysates of HTLV-III were fractionated by SDS (sodium dodecyl sulfate)-polyacrylamide slab gel electrophoresis. The proteins were electrophoretically transferred to nitrocellulose sheets according to Towbin et al (12'). The sheets were incubated at 37° C. for 3 hours with 5% bovine serum albumin (BSA) in 10 mM Tris HCl, Ph 7.4, containing 0.9% NaCl and cut into strips. Each strip was incubated for two hours at room temperature and overnight at 4° C. with 1:1000 dilution of conventional control serum or 1:10 dilution of spent supernatant fluid from hybrids. The incubation buffer (buffer I) consisted of 20 mM Tris HCl, 1 mM phenylmethylsulfonyl fluoride (PMSF) Ph 7.4, 1 mM EDTA, 0.2M NaCl, 0.3% Triton X-100 and 2 mg/ml of BSA. After the incubation, the strips were washed three times with 10 mM Tris-HCl, pH 7.4, 0.9% NaCl, 0.5% Triton X-100, 0.3% sodium deoxycholate, and 1mM EDTA. The strips were incubated at room temperature with buffer I containing 4% normal goat serum. $^{125}$I-labeled goat antibody ($5 \times 10^5$ cpm/ml) to mouse IgG, heavy and light chain specific, (N. L. Cappell Labs., Inc., Cochranville, Pa., USA) was added to the incubation mixture for 30 minutes. The strips were washed three times as before, briefly dried and exposed for autoradiography.

INDIRECT IMMUNOFLUORESCENCE ASSAY

The assays were carried out on fixed cells as described (37'). Briefly, H9 and H9/HTLV-III cells were spotted on slides, air dried and fixed for 10 minutes in 50% methanol:50% acetone. Supernatant fluid or ascites from each individual hybridoma was applied to cells and incubated 30 minutes at room temperature. FITC-labeled goat anti-mouse IgG F(ab')$_2$ (N. L. Cappell Labs., Inc.) was used to detect reactive cells.

P24 MONOCLONAL ANTIBODIES

Figure 1:
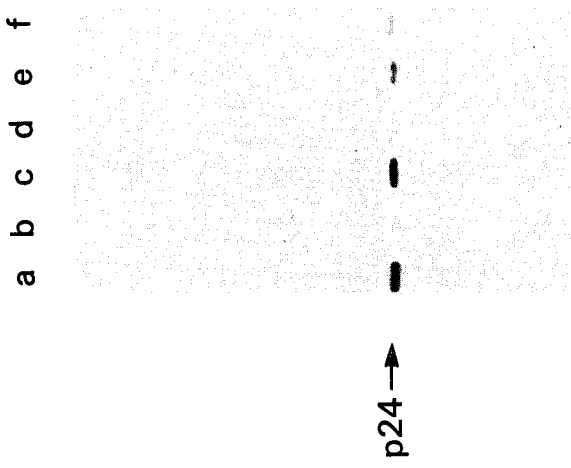

Of the several hundred hybridoma fluids tested, four, each from an independent fusion, were found to secrete antibody specific for a protein with a molecular weight of 24,000 in HTLV-III preparations as shown in FIG. 1. The monoclonals designated SVM-16, SVM-23, and SVM-26 reacted with different titers against p24 as determined by comparison to a hyperimmune mouse antiserum. All the hybridomas were highly stable through repeated cycles of subcloning. We determined the immunoglobulin subclass secreted by each as an initial step in establishing the monoclonality and because of the functional significance of the different classes of immunoglobulins. SVM-16 synthesized IgM; SVM-23 synthesized IgG$_2$, SVM-25, SVM-26, and SVM-33 synthesized IgG$_1$. All monoclonals had kappa light chains. Immunoglobin characterization was established by conventional immunological procedures, including Ouchterlony analysis of concentrated culture supernatants using specific typing sera and by SDS-polyacrylamide gel analysis of [$^3$H]-leucine labeled secreted products.

The identity of the protein recognized by these hybridomas as viral encoded gene product was confirmed by comparing the reactivities of individual hybridomas with lysates of one immortalized and infected human T-cell clone, H9/HTLV-III, and with lysates of the same clone before viral infection, H9. Representative results are shown in FIG. 2 for "p24" hybridomas. P24 was recognized in the HTLV-III purified preparation and in the cellular H9/HTLV-III lysate, but it was not present in the uninfected H9 control, thus confirming the specificity of the reaction. The different titers of reactivities are due to the extensive accumulation of p24 in the virus preparation. All p24 hybridomas also recognized two other proteins higher than p24 in the cellular preparation, likely group specific antigen gag-protein precursors. Both B and SVM-23 also immunoprecipitated $^{125}$I-labeled purified HTLV-III p24.

Only very limited cross-reaction of HTLV-III p24 with HTLV-I and -II p24 has already been reported (33'), supporting the uniqueness of HTLV-III. It was of interest then to examine whether the antigenic sites recognized by the four p24 hybridomas in the p24 sequence were in the region of homology or non-homology among the three isolates. Representative results are shown in FIG. 3. It is evident that the reactive epitopes are type specific since they are not shared with HTLV-I and -II or cells producing HTLV-I or -II. All the hybridomas raised so far against HTLV-I and -II p24s recognized instead common epitopes, supporting our conclusion of more extensive homology in the sequence of this protein between HTLV-I and -II. The p24 monoclonal antibodies demonstrated additional specificity for HTLV-III p24, as they were not reactive with phytohemagglutinin stimulated normal human lymphocytes or with various human B cell lines.

The potential usefulness of these hybridomas as diagnostic tools was further verified in indirect immunofluorescence assays. All four p24 hybridomas specifically labeled only HTLV-III producing cells. The uninfected H9 cells did not produce HTLV-III and were negative for p24. Only fixed cells were labeled, supporting the notion that p24 is an internal structural component of HTLV-III (32'). The fluorescent staining of virus positive cells was restricted to the plasma membrane. The percentage of reactivity of positive p24 hybrids varied. Unconcentrated culture fluids from SVM-23 labeled 60% of H9/HTLV-III cells, while fluids from SVM-16 labeled only 20–30% of the cells, and then only after ten-fold concentration or as ascitic fluid.

These results demonstrate the production and characterization of the first specific monoclonal immunologic reagents to HTLV-III p24. The specificity of the reaction was analyzed by several methods including immune transfer (Western blot) and indirect immunofluorescence. The antigenic determinants recognized were defined as type specific since there was no cross-reaction with either HTLV-I and -II p24s. Thus, the p24 hybridomas provide an immediate method to assay for HTLV-III expression in a variety of tissues. These reagents will be useful as diagnostic tools in early stages of the disease when the patient's T-cell repertoire is not yet compromised and when therapy can be more effective. Moreover, virus has been isolated from antibody negative individuals (38'), demonstrating that direct detection methods using these novel monoclonal antibodies are effective when the indirect methods used to date which measure the presence of natural antibodies are of no use. Since virus isolation cannot be routinely employed in large numbers, the use of an immunoassay specific for a virus antigen provides an improved reagant for use in screening for virus infection in a population or for detection of virus in blood products.

GP41 MONOCLONAL ANTIBODIES

Supernatants of hybrids which showed positive reactions in ELISA tests with HTLV-III proteins were further assayed by immunoblot techniques to assess defined specificity to HTLV-III gp41, a 41K (41,000) dalton glycoprotein antigen recognized by AIDS patient sera. Of the several hybridomas tested, one, designated SVM-25, secreted antibodies specific for gp41 in HTLV-III preparations (FIG. 4B). The antibody did not react with cells not infected with HTLV-III.

Figure 5:
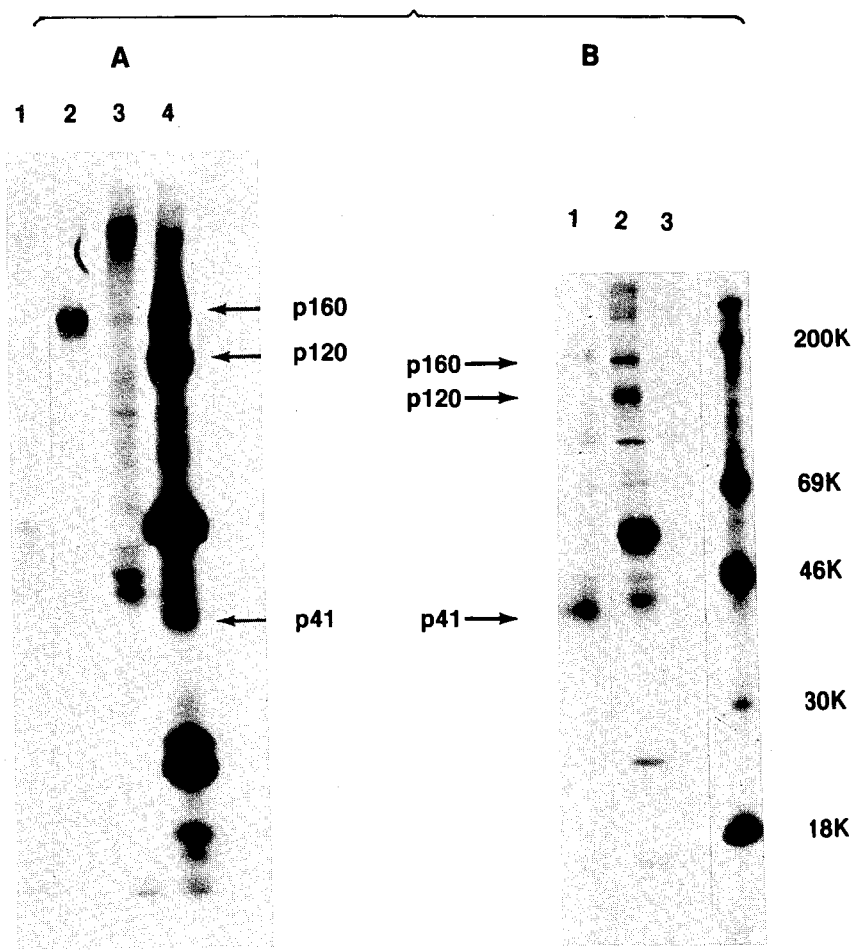

To characterize the protein reactive with monoclonal antibody SVM-25, lysates of HTLV-III producing cells were immunoprecipitated and analyzed by sodium dodecylsulfate-polyacrylamide gel electrophoresis (SDS-PAGE). Growing cultures of H9/HTLV-III were labeled with [$^3$H]-leucine, [$^3$H]-isoleucine, or [$^{35}$S]-cysteine in separate experiments. The washed cells were lysed with a mixture of detergents and the clarified extracts were treated overnight with ascitic fluids from SVM-25 or an antibody-positive human serum. The precipitates were collected and, after extensive washing, were boiled with SDS-beta-mercaptoethanol and analyzed by SDS-PAGE. Results obtained with extracts of [$^3$H]-leucine and [$^{35}$S]-cysteine-labeled cells are shown in FIG. 5. As expected, the human serum precipitated a large number of viral proteins, including the group specific antigen gag proteins p17, p24, and the gag precursor p53 (15′), in addition to gp41 and two large molecular weight proteins (p160 and p120) that we and others had speculated earlier to be related to HTLV-III envelope (15′,16′). With [$^3$H]-leucine-labeled extract the reactivity of SVM-25 was mainly directed against gp41, with additional reaction to p160 (PANEL B). The pattern with [$^3$H]-isoleucine-labeled cells was identical to that with [$^3$H]-leucine-labeled cells. When proteins were labeled with [$^{35}$S]-cysteine, p160 was the predominant antigen detected (PANEL A). Gp41 is only weakly detected with this label and required long exposure of autoradiogram. However, in none of the experiments was p120 detected by the gp41 monoclonal antibody. This pattern is consistent with p160 being a precursor of gp41 and with the epitope specified by SVM-25 being located in the gp41 region of the precursor.

Monoclonal antibody SVM-25 reacted with antigens on the surface of H9/HTLV-III cells in live cell membrane immunofluorescence assays (17′), suggesting that gp41 might be a component of the envelope of HTLV-III. To further characterize gp41, we immunoprecipitated it from [$^3$H]-leucine and [$^3$H]-isoleucine-labeled H9/HTLV-III cell extracts, and subjected it to radiolabel sequencing by Edman degradation. The [$^3$H]-leucine labeled gp41 band (FIG. 5A) and [$^3$H]-isoleucine labeled gp41 band (not shown), as identified by autoradiography were sliced out of the polyacrylamide gel and eluted with distilled water containing 10 nmoles of sequence grade sperm whale apomyoglobin (Beckman). Each sample was transferred to a prewashed dialysis bag and dialysed at 4° C. against 3 changes of 5% acetic acid (2 liters each). An aliquot was removed for counting and the remainder was utilized for N-terminal sequence anaylsis. The protocols followed for radiolabeled semiautomated Edman degradation in a Beckman spinning cup sequenator were those described elsewhere (18′). Ten percent of cycles 2 and 9 were removed, processed and analyzed for the phenythiohydantoin derivative of leucine found in myoglobin at these two positions. The anilinethiazolinone amino acids in n-chlorobutane were transferred to scintillation vials, dried with N$_2$ and a heat lamp and redissolved in 10 ml Aquasol (New England Nuclear). Each fraction was counted for 20 minutes. The results of the sequence analysis are presented in FIG. 6. Isoleucine was unambiguously assigned at position 4 of the 24 cycles examined (FIG. 7A). Leucine occurred in cycles 7, 9, 12, 26, 33, and 34 out of 40 cycles analyzed (FIG. 7B). The amino acid sequence determined prefectly matched the predicted sequence (4′) and it precisely located gp41 in the envelope-long open reading frame (env-lor) gene of HTLV-III provirus clones BH-10 and BH-8 (4′). The probability of having the observed identities occur by chance is $1.5 \times 10^{-10}$. The absence of additional radioactive residues from sequencing analysis indicated that gp41 isolated by immunoprecipitation with the monoclonal antibody SVM-25 was radiochemically homogeneous.

The use of the monoclonal antibody SVM-25 has enabled us, for the first time, to definitively identify the primary env-gene product of HTLV-III and to understand its processive cleavage pattern. The observation that the gp41 antibody precipitated a p160 and a gp41 from cell extracts, while only gp41 was recognized in viral extracts by the immunoblot technique, demonstrates that p160 is the primary cellular translational product and gp41 is one of the products of processing during viral maturation. Radiolabeled amino acid sequencing has identified gp41 as the COOH-terminal fragment generated by cleavage of p160 between Arg$^{518}$ and Ala$^{519}$, as in the deduced amino acid sequence of the env-lot gene product (FIG. 8) (4′). Thus, gp41 is the transmembrane protein of HTLV-III. Examination of the nucleotide sequence identifies hydrophobic domains in gp41, as also seen in other retroviral homologs (19′). The cleavage site identified by the amino acid sequence analysis was similar to those in other retroviral envelope gene (env-gene) products (19′). The predicted size of a single polypeptide starting with Ala$^{519}$ and extending to Leu$^{863}$, and containing 6 potential glycosylation sites, would be much larger than 41K daltons, provided that all potential sites are glycosylated. Since gp41 was experimentally identified as a glycoprotein (13′), at least some of these sites are glycosylated. This implies that some further processing occurs at the C-terminal end of the primary env-lor product to generate gp41. Further sequence analysis of gp41 will be necessary to precisely locate such processing sites.

Figure 7:
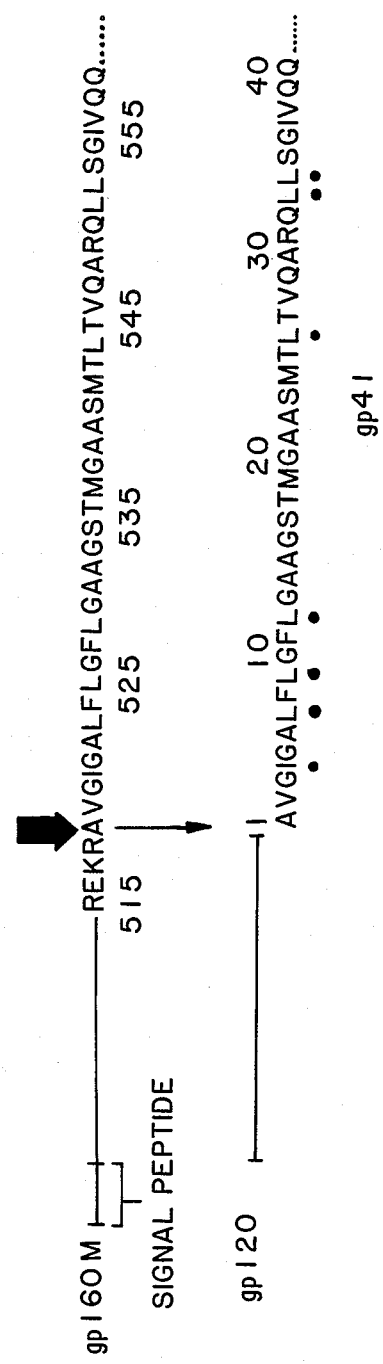

The NH$_2$-terminal fragment of the primary cleavage of p160 should be p120, which was not recognized by the gp41 monoclonal SVM-25, but was readily identified in both the cellular extracts and in viral lysates by sera of HTLV-III-antibody-positive individuals (FIGS. 4, 5; Reference 13′,15′,16′). This conclusion is in keeping with the finding of common amino acid sequences between p120 and p160 by peptide mapping (15′), and identical NH$_2$-terminal amino acid sequences between p120 and p160 by Edman degradation (20′). The gp100 described by Hunsmann et al (21′) has the same NH$_2$-terminal sequence as p120 and p160 (22′) and may be the same as p120 described by others. The proposed scheme for the processing of the primary env-lor product is depicted in FIG. 7.

DETAILED DESCRIPTION OF THE FIGURES

FIG. 1. Analysis of supernatants from four individual hybridomas for binding to HTLV-III p24. Strips were prepared as described with HTLV-III (5 μg/lane) and reacted with 1:10 dilution of culture fluid from each individual hybridoma or a 1:1000 dilution of positive or negative sera.

Lane a, hyperimmune mouse antiserum to HTLV-III p24; lane b, prebleed of the same mouse as negative control; lanes e and f, supernatants from hybridomas SVM-16 and SVM-23, respectively.

FIG. 2. Specificity of the SVM-16 hybridoma recognition of p24 in HTLV-III and in HTLV-III producing cells. Strips were prepared with HTLV-III (5 µg/lane), H9 and H9/HTLV-III extracts (200 µg/lane) as described and reacted with 1:10 dilution of culture fluid from each individual hybridoma. Hybridomas SVM-16, SVM-23, and SVM-26 gave similar patterns of reactivity. Lane a, H9/HTLV-III producer line; lane b, H9 non-producer line; lane c, HTLV-III.

FIG. 3. Western blot analysis with the SVM-16 hybridoma of antigenic cross-reactivities of HTLV-III p24 with HTLV-I and -II. Lysates of HTLV-III (lane a); HTLV-I and -II (lanes b,c); HTLV-I and -II producing cells, namely HUT 102 and C3-44 (lanes d,e); a human B lymphoblastoid line called CR-B (lane f); and mitogen stimulated human T cells (lane g) were analyzed by the Western blot technique. Hybridomas SVM-16, SVM-23 and SVM-26 gave the same pattern of reactivity. [$^{14}$C]-labeled molecular weight standards include phosphorylase B (92,500), bovine serum albumin (69,000), ovalbumin (46,000), carbonic anhydrase (30,000) and lactoglobulin A (18,700).

FIG. 4. Detection of HTLV-III gp41 by human sera and a mouse monoclonal antibody in the immunoblot assay. Lysates of HTLV-III were fractionated by SDS-polyacrylamide gel electrophoresis. The proteins were electrophoretically transferred to nitrocellulose sheets according to Towbin et al (12'). These sheets were then incubated for 8 hours at 37° C. in a 5% solution of non-fat dry milk containing 0.01% Antifoam (Sigma) and 0.0001% Merthiolate (blocking medium) to block nonspecific protein binding sites. Strips were cut from these sheets containing a representative profile of viral antigens and incubated in individual test tubes with 2.5 ml of blocking medium containing 4% normal goat serum and 25 µl of the human test serum, or mouse mononclonal antibody in ascitic form. The strips are washed three times with 0.5% sodium deoxycholate, 0.1M NaCl, 0.5% Triton X-100, 1 mM 2MSF, and 10 mM sodium phosphate (wash medium). The washed strips are incubated for 30 minutes in 2.5 ml of blocking medium containing 4% normal goat serum with $2.5 \times 10^6$ cpm of $^{125}$I-labeled goat IgG reactive against human IgG, or mouse IgG as appropriate. The strips were washed again as before, dried, mounted, and autoradiographed. Panel A: lane 1, serum from a negative human control; lanes 2, 3 and 4, sera from AIDS patients. Panel B: lane 1, ascitic fluid from P3 as negative control; lane 2, ascitic fluid form SVM-25.

FIG. 5. Immunoprecipitation of metabolically labeled HTLV-III proteins by AIDS sera and monoclonal antibody to HTLV-III gp41 (SVM-25). Tissue culture cells were radioactively labeled by incubation for 8 ([$^{35}$S]-cysteine) to 18 ([$^3$H]-leucine and [$^3$H]-isoleucine) hours in medium containing either [$^{35}$S]-cysteine, [$^3$H]-leucine or [$^3$H]-isoleucine (100 µl/ml). Labeled cells were washed twice in serum-free RPMI medium and disrupted at 4° C. by repeated aspiration through a 25-gauge needle in 10 mM sodium phosphate (pH 7.2), containing 0.5% NaCl, 1% Triton X-100, 0.5% sodium deoxycholate and 0.1% SDS (PBS-TDS). The lysates were preabsorbed for 3 hours at room temperature with protein A-Sepharose and aliquots of normal sera. Immunoprecipitation analysis was performed by addition of either 1.0 µl of ascites fluid, or 10 µls of human sera, 0.2 ml of rabbit anti-mouse K light chain only in the sample containing mouse monoclonal antibody and 0.2 ml of 10% suspension of protein A-Sepharose to 1 ml of labeled and clarified extract. The samples were incubated for 18 hours at 4° C. Immunoprecipitates were collected by centrifugation at 2,000 xg for 10 minutes, washed repeatedly in PBS-TDS, suspended in 50 µl of 0.65 M Tris-hydrochloride (pH 6.7), 1% SDS, 10% glycerol, 2.5% 2-mercaptoethanol, and 0.1% bromophenol blue, heated for 2 minutes at 90° C., and analyzed by SDS-PAGE. Panel A: [$^{35}$S]-cysteine labeled cells. Lane 1, ascitic fluid from P3 as negative control; lane 2, ascitic fluid from SVM-25; lane 3, negative human control serum; lane 4, serum from an AIDS patient. Panel B: [$^3$H]-leucine labeled H9/HTLV-III cells. Lane 1, ascitic fluid from SVM-25; lane 2, serum from AIDS patient, lane 3, negative human control serum.

Figure 6B:
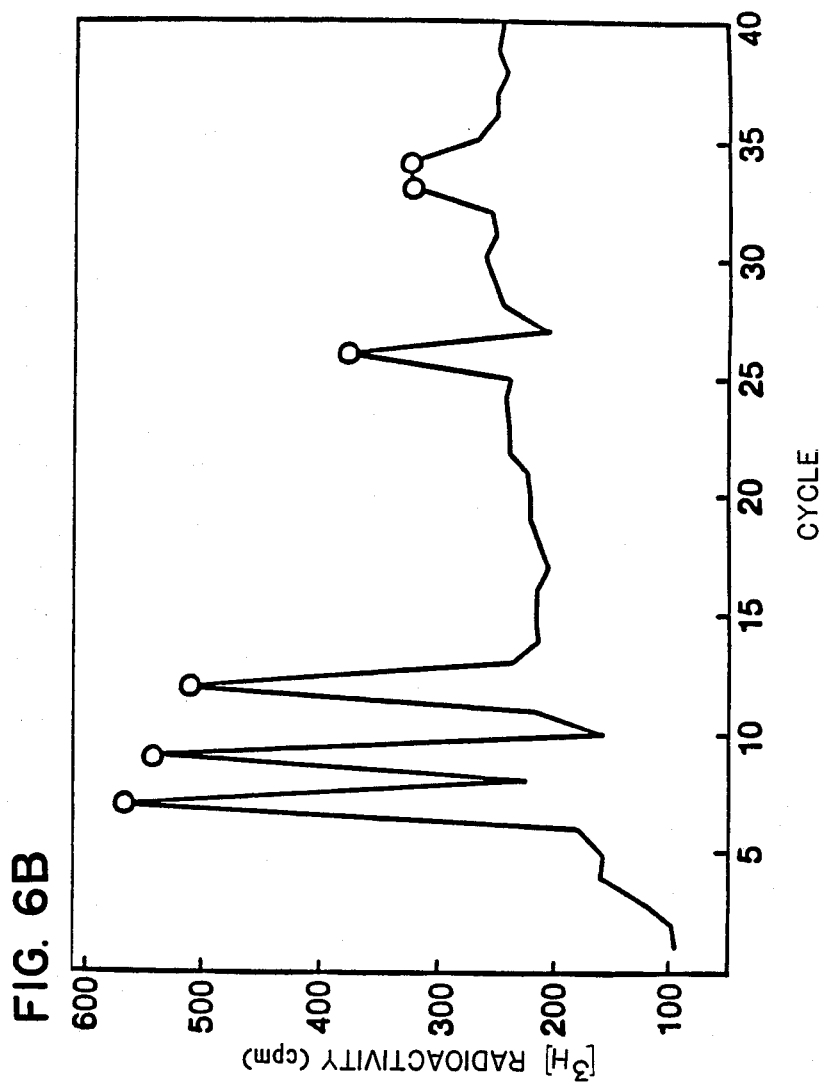

FIG. 6. Amino terminal sequence analysis of [$^3$H]-isoleucine-(A) and [$^3$H]-leucine (B)-labeled gp 41. H9/HTLV-III cells were labeled with the radioactive amino acids and the labeled gp 41 was isolated from cell extract by immunoprecipitation with the monoclonal antibody SVM-25, as described in the legend to FIG. 5. The radioactive gp41 band was identified by autoradiography and was sliced out of the gel and eluted with water as described in the text. The dialyzed proteins in the presence of apomyoglobin were subjected to semi-automated Edman degradation. The recovery of reactivity in each cycle is given in the Figure. Positive identifications are indicated by the open circles. Isoleucine was found in position 4 while leucine was found in positions 7, 9, 12, 26, 33, and 34.

FIG. 7. Diagram representing the processing of the primary env-lor gene product into gp120 and gp41. Numbers below the amino acid sequence of gp160 denote the positions in the deduced amino acid sequence for the primary gene product. Bold arrow indicates the identified cleavage site. Amino acid residues identified by asterisks are those determined by radiolabel sequence analysis (see FIG. 7). Numbers above the amino acids in gp41 denote the degradation cycle of the sequencing procedure.

REFERENCES

1'. M. Popovic, M. G. Sarngadharan, E. Read, R. C. Gallo, Science 224, 497 (1984); R. C. Gallo et al., ibid., 224, 500 (1984); S. Z. Salahuddin et al., Proc. Natl. Acad. Sci. USA, in press.

2'. F. Barré-Sinoussi et al., Science 220, 868 (1983).

3'. E. Vilmer et al., Lancet 1, 753 (1984); J. A. Levy et al., Science 225, 840 (1984).

4'. L. Ratner et al., Nature 313, 227 (1985).

5'. S. Wain-Hobson, P. Sonigo, O. Danos, S. Cole, M. Alizon, Cell 40, 9 (1985); R. Sanchez-Pescador et al., Science 227, 484 (1985).

6'. G. M. Shaw, B. Hahn, S. K. Arya, J. E. Groopman, R. C. Gallo, F. Wong-Staal, Science 226, 1165 (1984); M. Alizon et al., Nature 312, 757 (1984).

7'. M. G. Sarngadharan, M. Popovic, L. Bruch, J. Schüpbach, R. C. Gallo, Science 224, 506 (1984); B. Safai, M. G. Sarngadharan, J. E. Groopman, M. Popovic, J. Schüpbach, K. Arnett, A. Sliski, R. C. Gallo, Lancet 1, 1438 (1984).

8'. Cheingsong-Popov et al., Lancet 2, 477 (1984); F. Brun-Vézinet et al., ibid., 1, 1253 (1984); S. H. Weiss et al at J. Am. Med. Assoc. 253, 221 (1985).

9'. H. W. Jaffe, M. G. Sarngadharan, A. Devico, L. Bruch, J. P. Getchell, V. S. Kalyanaraman, H. W.

Haverkos, R. L. Stoneburner, R. C. Gallo, J. W. Curran, manuscript submitted for publication.
10'. M. Popovic, E. Read-Connole, R. C. Gallo, *Lancet* 1, 1437 (1985); A. G. Dalgleish et al., *Nature* 312, 763 (1984); D. Klatzmann et al., ibid., 312, 767 (1984).
11'. D. D. Ho et al., *Science* 226, 451 (1984); D. Zagury et al., *Science* 226, 449 (1984); J. E. Groopman et al., ibid., 226, 447 (1984).
12'. H. Towbin, T. Staehelin, J. Gordon, *Proc. Natl. Acad. Sci, USA,* 76, 4350 (1979).
13'. M. G. Sarngadharan, F. diMarzo Veronese, S. Lee, R. C. Gallo, *Cancer Res.* in press.
14'. C. L. Reading, *J. Immunol. Methods* 53, 261 (1982).
15'. W. G. Robey, B. Safai, S. Oroszlan, L. O. Arthur, M. A. Gonda, R. C. Gallo, P. J. Fischinger, *Science* 228, 593 (1985); F. deMarzo Veronese et al., Manuscript in preparation.
16'. L. Kitchen et al., *Nature* 312, 3367 (1984); R. C. Gallo et al., in *Progress in Allergy,* Vol. 37, E. Klein, Ed. (S. Karger, Basel, Switzerland) in press; F. Barin, M. F. McLane, J. S. Allan, T. H. Lee, J. E. Groopman, M. Essex, submitted for publication.
17'. Our unpublished data.
18'. T. Y. Shih, P. E. Stokes, G. W. Smythers, R. Dhar, and S. Oroszlan, *J. Biol. Chem.* 257, 11767 (1982).
19'. T. M. Shinnick et al., *Nature* 293, 543 (1981); L. E. Henderson et al., *J. Virol.* 52, 492 (1984); M. S. Seiki et al., *Proc. Natl. Acad. Sci. USA,* 80 3618 (1983); T. H. Lee et al., ibid., 81 7579 (1984); N. R. Rice et al., *Virology,* 138, 82 (1984); A. M. Schultz et al.,
20'. J. S. Allan, J. E. Coligan, F. Barin, M. F. McLane, J. G. Sodrosky, C.A. Rosen, W. A. Haseltine, T. H. Lee, M. Essex, submitted for publication.
21'. J. Schneider, H. Boyer, V. Bienzle, G. Hunsmann, *Med. Microbiol. Immunol.,* in press.
22'. G. Hunsmann, personal communication.
23'. Poiesz, B. J., Ruscetti, F. W., Gazdar, A. F., Bunn, P. A., Minna, J. D. and Gallo, R. C. (1980) *Proc. Natl. Acad. Sci. USA* 77, 7415–7419.
24'. Gallo, R. C. (1984) in *Cancer Surveys,* eds. Franks, L. M., Wyke, L. M. and Weiss, R. A. (Oxford University Press, Oxford), pp. 113–159.
25'. Kalyanaraman, V. S., Sarngadharan, M. G., Robert-Guroff, M., Miyoshi, I., Blayney, D., Golde, D. and Gallo, R. C. (1982) *Science* 218, 571–573.
26'. Feorino, P. M., Kalyanaramam, V. S., Haverkos, H. W., Cabradilla, C. D., Warfield, D. T., Jaffe, H. W., Harrison, A. K., Gottlieb, M. S., Goldfinger, D., Chermann, J. C., Barre-Sinoussi, F., Spira, T. T., McDougal, J. S., Curran, J. W., Montagnier, L., Murphy, F. A. and Francis, D. P. (1984) *Science* 225, 69–72.
27'. Gottlieb, M. S., Schroff, R., Schanker, H. M., Weisman, J. D., Fau, P. T., Wolf, R. A. and Saxon, A. (1981) *N. Engl. J. Med.* 305, 1425–1431.
28'. Siegal, F. P., Lopez, C., Hammer, G. S., Brown, A. E., Kornfeld, S. J., Gold, J., Hasset, J., Hirschman, S. Z., Cunningham-Rundles, C., Adelsberg, B. R., Parham, D. M., Seigal M., Cunningham-Rundles, S. and Armstrong, D. (1981) *N. Engl. J. Med.* 305, 1439–1444.
29'. Centers for Disease Control Task Force on Kaposi's Sarcoma and Opportunistic Infections (1983) *N. Engl. J. Med.* 306, 248–252.
30'. Popovic, M., Sarin, P. S., Robert-Guroff, M., Kalyanaraman, S. V., Mann, D., Minowada, J. and Gallo, R. C. (1983) *Science* 219, 856–859.
31'. Markham, P. D., Salahuddin, S. Z., Macchi, B., Robert-Guroff, M. and Gallo, R. C. (1984) *Int. J. Cancer* 33, 13–17.
32'. Schüpbach, J. Popovic, M., Gilden, R., Gonda, M. A., Sarngadharan, M. G. and Gallo, R. C. (1984) *Science* 224, 503–505.
33'. Sarngadharan, M. G., Bruch, L., Popovic, M. and Gallo, R. C. (1985) *Proc. Natl. Acad. Sci, USA* 82, 3481–3484.
34'. Arya, S. K., Gallo, R. C., Hahn, B., Shaw, G., Popovic, M., Salahuddin, S. Z. and Wong-Staal, F. (1984) *Science* 225, 927–930.
35'. Shaw, G. M., Hahn, B., Arya, S. K., Popovic, M. Groopman, J. E., Gallo, R. C. and Wong-Staal, F. (1984) *Science* 225, 1473–1476.
36'. Galfre, G., Howe, S. C., Milstein, C., Butcher, G. W. and Howard, J. C. (1977) *Nature* (London) 266, 550–552.
37'. Robert-Guroff, M., Nakao, Y., Notake, K., Ito, Y., Sliski, A. and Gallo, R.C. (1982) *Science* 215, 975–978.
38'. Salahuddin, S. Z., Groopman, J. E., Markham, P. D., Sarngadharan, M. G., Redfield, R. R., McLane, M. F., Essex, M., Sliski, A. and Gallo, R. C. (1984) *Lancet* 2, 1418–1420.

What is claimed is:

3. A monoclonal antibody produced by the hybridoma cell line of claim 1, said antibody having binding specificity for epitopes on HTLV-III proteins selected from the group consisting of p41, p24 and p17.

4. The monoclonal antibody of claim 3, having essentially no cross-reactivity with HTLV-I and HTLV-II proteins.

5. The monoclonal antibody of claim 3, selected from the group consisting of SVM-16, SVM-23, SVM-25, SVM-26 and SVM-33.

6. The monoclonal antibody of claim 3, having binding specificity for an epitope on HTLV-III virus protein p17.

10. The monoclonal antibody of claim 3, having binding specificity for an epitope on HTLV-III virus protein p24.

8. The monoclonal antibody of claim 3, having binding specificity for an epitope on HTLV-III virus glycoprotein gp41.

7. The monoclonal antibody of claim 4, consisting of SVM-33, having the immunoglobin subclass IgG$_1$.

11. The monoclonal antibody of claim 10, consisting of SVM16, having the immunoglobin subclass IgM.

12. The monoclonal antibody of claim 10, consisting of SVM-23, having the immunoglobin subclass IgG$_2$.

13. The monoclonal antibody of claim 10, consisting of SVM-26, having the immunoglobin subclass IgG$_1$.

9. The monoclonal antibody of claim 8, consisting of SVM-25, having the immunoglobin subclass IgG$_1$.

1. A hybridoma cell line that produces a monoclonal antibody having binding specificity for epitopes on HTLV-III proteins selected from the group consisting of p41, p24 and p17.

2. The hybridoma cell line of claim 1, selected from the group consisting of MH-SVM-16 (ATCC accession number HB 8880), MH-SVM-23 (ATCC accession number HB 8870), MH-SVM-25 (ATCC accession number HB 8871), MH-SVM-26 (ATCC accession number HB 8872) and MH-SVM-33 (ATCC accession number HB 8975).

* * * * *